(12) United States Patent
Schlüssel et al.

(10) Patent No.: US 8,845,327 B2
(45) Date of Patent: Sep. 30, 2014

(54) CASTING ABUTMENT FOR A DENTAL IMPLANT

(75) Inventors: Marcel Schlüssel, Basserdorf (CH); Holger Kast, Lörrach (DE); Fabian Schwieder, Basel (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 11/983,246

(22) Filed: Nov. 8, 2007

(65) Prior Publication Data

US 2008/0153066 A1 Jun. 26, 2008

(30) Foreign Application Priority Data

Nov. 10, 2006 (EP) .................................. 06123857

(51) Int. Cl.
*A61C 13/36* (2006.01)
*A61C 13/38* (2006.01)
*A61C 8/00* (2006.01)

(52) U.S. Cl.
CPC .............. *A61C 8/005* (2013.01); *A61C 8/0069* (2013.01); *A61C 8/0066* (2013.01)
USPC .......................................... 433/172; 433/213

(58) Field of Classification Search
USPC .............. 433/172–176, 191–195, 201.1, 206, 433/214, 220, 221, 213
See application file for complete search history.

(56) References Cited

U.S. PATENT DOCUMENTS

| | | | | |
|---|---|---|---|---|
| 626,738 A * | 6/1899 | Underwood | .................. | 433/221 |
| 4,480,997 A * | 11/1984 | Deutsch et al. | ............... | 433/221 |
| 4,758,161 A * | 7/1988 | Niznick | ........................ | 433/173 |
| 5,259,759 A * | 11/1993 | Jorneus et al. | ................ | 433/173 |
| 5,556,280 A * | 9/1996 | Pelak | .............................. | 433/172 |
| 5,662,473 A | 9/1997 | Rassoli et al. | | |
| 5,681,167 A * | 10/1997 | Lazarof | ......................... | 433/174 |
| 5,927,979 A * | 7/1999 | Misch et al. | .................. | 433/173 |
| 6,083,004 A * | 7/2000 | Misch et al. | .................. | 433/173 |
| 6,168,436 B1 * | 1/2001 | O'Brien | ......................... | 433/173 |
| 6,394,809 B2 * | 5/2002 | Rogers et al. | ................. | 433/174 |
| 6,655,962 B1 * | 12/2003 | Kennard | ....................... | 433/174 |
| 6,726,480 B1 * | 4/2004 | Sutter | ........................... | 433/173 |
| 7,137,816 B2 * | 11/2006 | Gervais et al. | ................ | 433/173 |
| 2003/0082499 A1 | 5/2003 | Engström et al. | | |
| 2003/0175655 A1 * | 9/2003 | Klardie et al. | ................ | 433/173 |
| 2004/0091838 A1 * | 5/2004 | Loertscher | .................... | 433/184 |
| 2006/0003287 A1 * | 1/2006 | Ose et al. | ........................ | 433/74 |

FOREIGN PATENT DOCUMENTS

| | | | |
|---|---|---|---|
| CA | 1148388 A | * | 6/1983 |
| DE | 197 42 381 A1 | | 2/1999 |
| JP | 0492658 | * | 3/1992 |
| WO | WO 99/17676 A | | 4/1999 |
| WO | WO 03/037207 A1 | | 5/2003 |

OTHER PUBLICATIONS

English language translation of DE 197 42 381 A1, Kirsch et al., Feb. 18, 1999.*

* cited by examiner

*Primary Examiner* — Todd Manahan
*Assistant Examiner* — Michael R Ballinger
(74) *Attorney, Agent, or Firm* — Scully, Scott, Murphy & Presser, P.C.

(57) ABSTRACT

A casting abutment for a dental implant comprising: an apical socket portion, a transition portion bordering coronally on the socket portion, an occlusal portion bordering coronally on the transition portion and having an apical lower rim, wherein the occlusal portion, starting from its lower rim, is provided on its peripheral surface with an area having indentations, whose crests face the transition portion.

10 Claims, 3 Drawing Sheets

CASTING ABUTMENT FOR A DENTAL IMPLANT

The present invention generally provides a casting abutment for a dental implant, preferably made of gold, with an improved connection to a modeling aid.

BACKGROUND OF THE INVENTION

In the art of dental implantology, abutments have become widely known. They are attached to the dental implant which was previously implanted in a patient's jaw bone. This is normally done by means of a screw joint, wherein torques within the range of 35 Ncm are used to connect the abutment to the dental implant.

In the manufacturing of a prosthesis, supports are frequently used which facilitate three-dimensional modeling of a precisely fitting dental prosthesis. There is the possibility of direct gating at a pre-formed casting abutment which most of the time consists of a gold alloy. This casting abutment is fixed to the implant or the implant analogue, respectively, by means of a screw. For achieving a clean screw channel during subsequent gating, a support, called in the following modeling aid and made of a plastic which can be burnt out, is plugged onto the casting abutment. This modeling aid can be modified as required.

For the manufacturing of the dental model, the desired shape of the individual secondary part is formed with a wax in the area of the collar of the casting abutment and the modeling aid, and subsequently a mold for casting is formed around the wax model according to methods well-known in the art. Then the modeling aid and the wax are burnt out for exposing the structure to be produced or the dental model as a die. A well-known method for producing these dies is lost-wax casting, wherein a die is manufactured, the wax is molten out during the casting process and the modeling aid is burnt without any residue. As a further step, a precious metal alloy is cast into this die through a cast channel, whereupon the highly liquid metal is flowing into the die and is attached to the surface of the casting abutment. At the same time, the die produced by the molten wax model is filled with the wax model copy.

Practice has shown that tightening of the occlusal screw for fixing the casting abutment to the dental model can cause tensions which may lead e.g. to a shift of the modeling aid in the vertical direction. This can cause formation of a gap between the casting abutment and the modeling aid, which gap is filled, during manufacturing of the casting pattern, with the encapsulant surrounding the modeling aid and the casting abutment. During gating, this area is not filled with metal, but remains occupied by the encapsulant so that the finished casting will have a gap, i.e. a casting error.

From SA-2003/9354, an abutment for dental implants is known wherein a (precious) metal cylinder is arranged on a dental implant, on whose occlusal end a plastic sleeve for manufacturing a socket is fastened. On its side facing the metal cylinder, the sleeve has an inner thread engaging a corresponding outer thread on the abutment for enabling casting of a metal post in the metal cylinder of the abutment and around the metal cylinder and for fixing it to the abutment. For a flawless casting process, the threaded joint must have very close tolerances in order to guarantee a very tight closure. In practice, these close tolerances can be achieved by means of fine threads which are, however, costly and very sensitive to handling.

SUMMARY OF THE INVENTION

Therefore, it is an object of the present invention to provide a casting abutment for a dental implant which avoids the above problems.

Within the framework of this object, a special task of the present invention is to implement a casting abutment for a dental implant which provides an enhanced connection to a modeling aid.

Furthermore, it is a special object of the present invention to provide a casting abutment for a dental implant which can be produced at a lower cost and with much less expenditure.

In addition, it is an object of the present invention to simplify assembly of the casting abutment for producing a dental model by means of a modeling carrier.

Also, it is an object of the present invention to expose the structure of the casting abutment during model production to forces which are as low as possible, or to transmit the forces during processing or modeling as well as possible, so that an employed modeling aid is not displaced from the casting abutment.

The above and other objects to be found in the following specification are achieved by a casting abutment according to the appended claims.

BRIEF DESCRIPTION OF THE DRAWINGS

Other features and advantages of the present invention as well as the mode of operation of the exemplary embodiment of the present invention are described below with reference to the accompanying drawings which illustrate the present invention and are intended to explain, together with the specification, the principles of the invention and to enable the person skilled in the art to manufacture and use the invention, wherein.

DESCRIPTION OF PREFERRED EMBODIMENTS

Figure 1A:
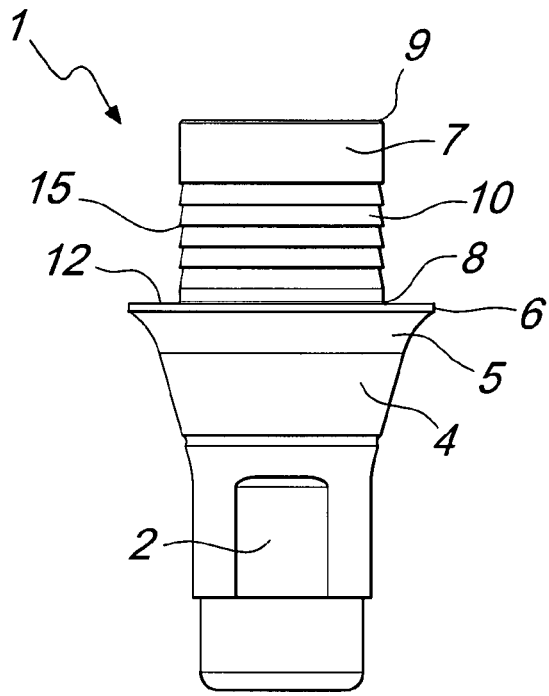
FIG. 1A shows a side or approximal view of a casting abutment according to an embodiment of the invention.
Figure 1B:
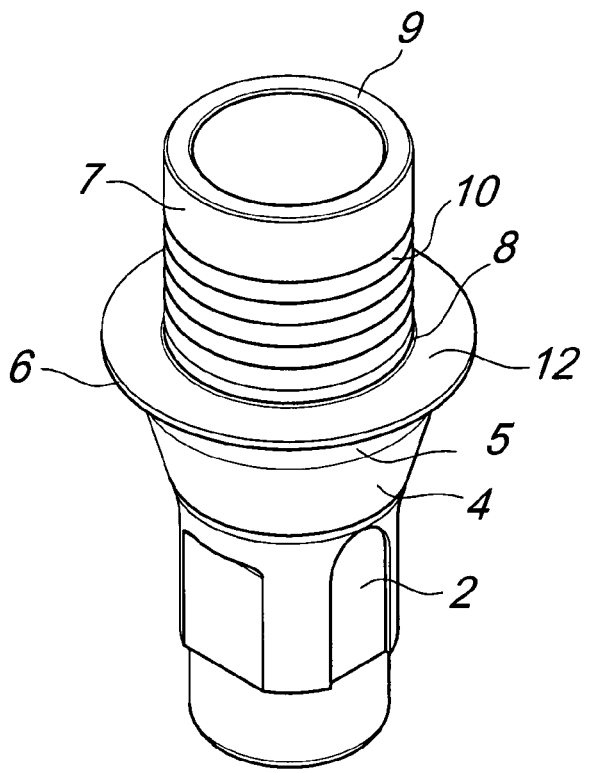
FIG. 1B shows an approximal view of a casting abutment according to FIG. 1A.
Figure 1C:
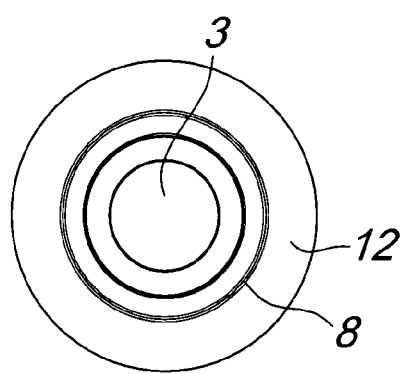
FIG. 1C shows a top view of the casting abutment according to FIG. 1A.

With reference to FIGS. 1A through 1C, a currently preferred embodiment of the casting abutment for a dental implant according to the present invention will be described. The casting abutment generally designated by reference number 1 has a socket portion 2 adapted to be received in a dental implant (not shown). The person skilled in the art will appreciate that the socket portion 2 has profiled areas in order to guarantee a precise fit or rotational securing of the casting abutment 1 with the implant. Moreover, the casting abutment 1, as known in the art, is provided with a through bore 3 adapted for receiving an occlusal screw (also not shown) to secure the casting abutment 1 to the dental implant fixed inside the jaw bone. During modeling of the dental model, the screw can further be used to fix the model on a modeling carrier (not shown) for machining. In the latter case, the screw is passed through the cylindrical bore 16 in the modeling aid 11 and screwed to the modeling carrier.

The socket portion 2 of the casting abutment 1 borders on a circular symmetric transition portion 4 which is preferably provided as a truncated cone. The transition portion 4 borders on an area 5 which, in the view shown in FIG. 1A, is provided with a planar rim 6.

The area designated by reference number 5 borders on a circular symmetric occlusal portion 7 of the casting abutment 1, a planar collar area 12 of even width being present between the planar rim 6 of the area 5 and the lower rim 8 of the circular symmetric occlusal portion 7, as can be clearly seen in FIG. 1B. The area of the occlusal portion 7 which borders on the lower rim 8 has, on its cylindrical outer surface, a plurality of stripe shaped or ring shaped indentations or tine like formations 10, which extend over an area of preferably approximately 75% of the cylinder area of the occlusal portion 7. Directly bordering on this, up to the upper rim 9, the surface of the occlusal portion 7 is smooth, permitting an easy placement of the modeling aid 11. The indentations 10, which are inclined downwards at an angle of preferably approximately 80° to the horizontal axis and whose ends form crests 15 facing the planar collar area 12, make it possible to force on a modeling aid 11 non-positively and tightly. During manufacturing of the dental model, the downwardly inclined crests 15 of the indentations 10 prevent a displacement or detachment of the modeling aid 11.

Figure 2A:
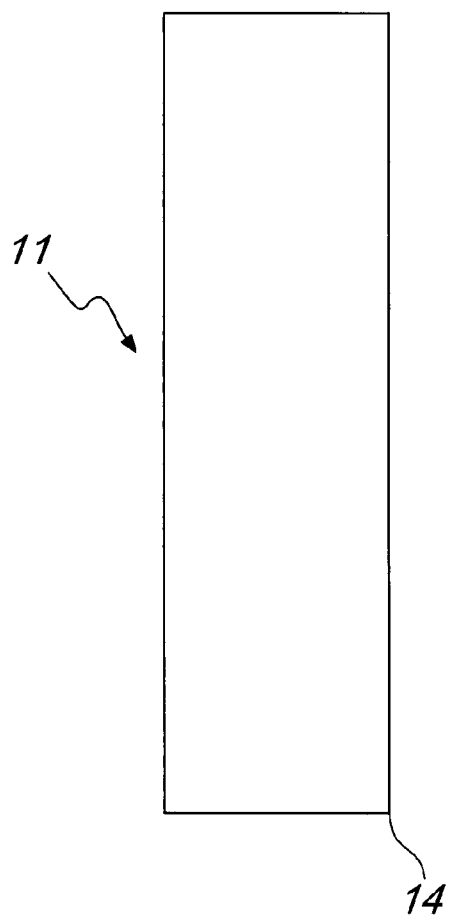
FIG. 2A shows an approximal view of a modeling aid according to FIG. 1A.
Figure 2B:
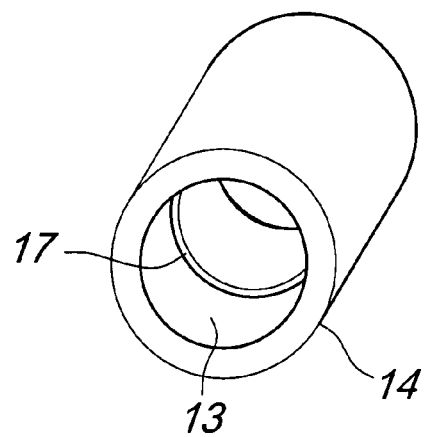
FIG. 2B shows a view of the modeling aid according to FIG. 2A from below at an angle.
Figure 2C:
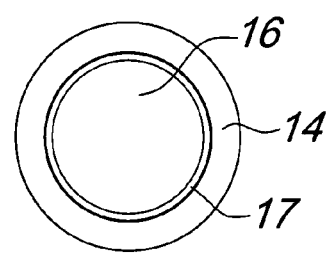
FIG. 2C shows a top view of the modeling aid according to FIG. 2A.

FIG. 2A shows the cylindrical modeling aid 11 which consists of combustible plastics and can be employed advantageously in combination with the casting abutment according to the invention. The modeling aid 11 has a smooth through bore 16 (see FIG. 2C) forming a channel for passing through the screw (not shown) which, after the dental model has been completed, is fastened to the patient's dental implant fixed inside the jaw bone. Inside the bore 16 which is designed to be plugged onto the casting abutment, a stop 17 is provided which, as shown in FIG. 2B, limits the distance a modeling aid 11 can be forced onto the cylindrical occlusal portion 7 when the stop 17 contacts the upper rim 9 of the casting abutment. Thus, advantageously, only a limited area 13 of the bore 16 of the modeling aid 11 is available for non-positive connection with the indentations 10, as is subsequently explained with reference to FIG. 3.

As explained above, the occlusal portion 7 of the casting abutment is cylindrical and has indentations 10, and therefore, according to the invention, a modeling aid 11 can be pressed on without any other aid. This enables manufacturing of casting abutments and modeling aids and prefabrication on a large scale.

According to the invention the tensions during modeling and manufacturing of the tooth, which are applied to the casting abutment and the modeling aid, do not lead to a shifting or sliding of the modeling aid.

Moreover, the invention produces an even and positive engagement between the collar area 12 of the casting abutment and the modeling aid 11, therefore preventing, after the casting process, a tedious and time-consuming finishing of the model which could even lead to destruction of the model.

Figure 3A:
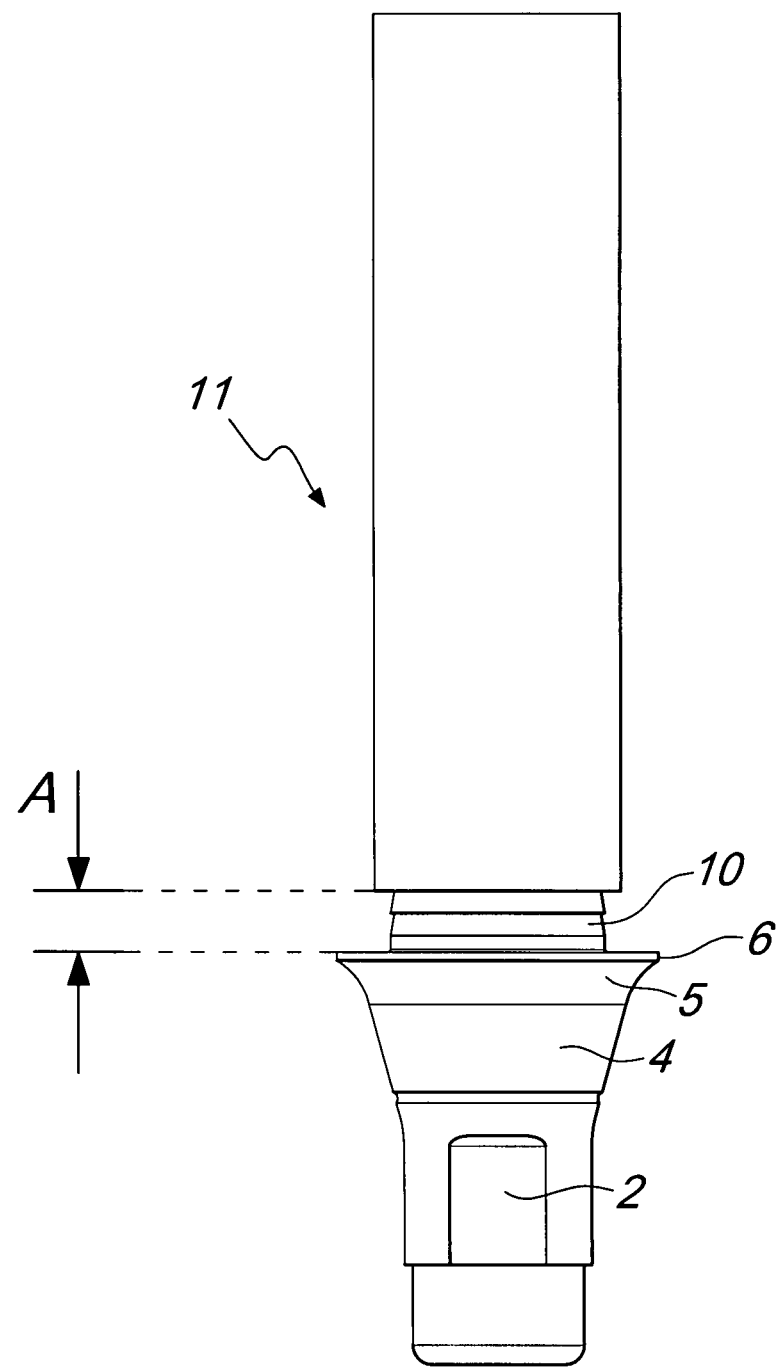
FIG. 3 shows a side or approximal view of the casting abutment according to the invention with the modeling aid forced onto the abutment.

FIG. 3 is a representation of a casting abutment with a forced-on modeling aid such as is used for manufacturing a dental model on a modeling carrier (not shown). When the modeling aid is pressed on, the distance surrounding the occlusal portion 7 of the casting abutment is limited by the stop 17 shown in FIG. 2B, creating a gap A between the lower edge 14 of the modeling aid and the collar area 12 of the casting abutment. This gap ensures good adhesion of the molding wax.

In particular, it has been noted in trials in connection with the gap A that an omission of the area between the collar area 12 of the casting abutment and the lower edge 14 of the plugged-on modeling aid 11, as shown in FIG. 3, can lead to an improvement of the quality and attachment of a precious metal applied in a gating process, preferably gold or highly precious alloys. This is due to the fact that during the gating process, the wax directly in contact with the casting abutment within the area of gap A is burnt out faster than the plastics of the modeling aid 11 so that gap A provides a space within which the heated plastics, which tends to swell up, can spread out. This minimizes tensions and cracks in the encapsulant or the mold and, consequently, flaws in the finished precious metal casting. In addition, even at the beginning of the gating process, the precious metal can penetrate at the casting abutment or casting abutment collar and establish contact with the same. Thus, the previously mentioned design of the modeling aid offers special advantages during the gating process for a precious metal.

Another advantage consists in that the total thickness of the molded wax can be lower within the area of gap A because of the missing modeling aid 11 since only the wax is present in this area. Therefore, the precious metal casting may be slimmer in the area of gap A, which leaves more room for subsequent formation of the dental prosthesis.

Although the invention has been described in connection with a one-piece casting abutment, the person skilled in the art will readily understand that it also applies to two-piece casting abutments, with naturally the same advantages being achieved as in connection with a one-piece casting abutment.

The disclosures in EPA No. 06123857.2 from which this application claims priority are incorporated herein by reference.

What is claimed is:

1. A combination of a modeling aid and a casting abutment for a dental implant,
    said casting abutment comprising:
        an apical socket portion that is adapted to be received in the dental implant,
        a transition portion bordering coronally on a socket portion, and
        an occlusal portion bordering coronally on the transition portion, the occlusal portion comprising an apical most rim, the entire occlusal portion being configured in a circular symmetric manner,
    wherein the occlusal portion comprises, on a peripheral surface thereof, a plurality of adjacent segments each of which has an exterior surface that tapers outwardly from a coronal end to an apical end, the plurality of adjacent segments extending coronally from the apical most rim of the occlusal portion,
    wherein the apical end of each segment has a diameter that is greater than a coronal end diameter of the apically adjacent segment, such that the segments collectively form a series of saw tooth-shaped crests that face the transition portion,
    wherein the modeling aid consists of combustible plastic and comprises a through bore, and the through bore of the modeling aid and/or the segments on the casting abutment are dimensioned so as to produce a non-positive engagement therebetween, and
    wherein the through bore of the modeling aid is provided with a stop on an inner surface of the modeling aid for limiting the distance by which said modeling aid is forceable onto the occlusal portion, such that a gap is created between the lower edge of the modeling aid and the apical most rim of the casting abutment, such that, in use, at least one segment is exposed.

2. The combination according to claim 1, wherein the transition portion is configured in a circular symmetric manner.

3. The combination according to claim 1, wherein the area of the peripheral surface of the occlusal portion having said segments takes up approximately 75% of the peripheral surface of the occlusal portion and wherein the remaining area of the peripheral surface of the occlusal portion is substantially smooth.

4. The combination according to claim 1, wherein the external surfaces of the segments are inclined downwardly at an angle of approximately 80° with respect to a horizontal axis of the occlusal portion.

5. The combination according to claim 4, wherein the segments are configured selectively in the form of stripes, rings, or tines.

6. The combination according to claim 1, wherein the segments are configured selectively in the form of stripes, rings, or tines.

7. The combination according to claim 1, wherein the modeling aid and the through bore thereof are configured substantially cylindrically.

8. The combination according to claim 1, wherein the occlusal portion is cylindrical.

9. The combination according to claim 1, wherein the apical socket portion, the transition portion and the occlusal portion are formed integrally.

10. The combination according to claim 1, further comprising a through bore adapted for receiving a screw to secure the casting abutment to the dental implant.

* * * * *